United States Patent
Hömberger et al.

(10) Patent No.: US 10,336,742 B2
(45) Date of Patent: Jul. 2, 2019

(54) PROCESS FOR PREPARING THIAZOLE DERIVATIVES

(71) Applicant: Bayer CropScience Aktiengesellschaft, Monheim am Rhein (DE)

(72) Inventors: Günter Hömberger, Eppstein (DE); Mark James Ford, Wiesbaden-Breckenheim (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/314,448

(22) PCT Filed: May 22, 2015

(86) PCT No.: PCT/EP2015/061455
§ 371 (c)(1),
(2) Date: Nov. 28, 2016

(87) PCT Pub. No.: WO2015/181097
PCT Pub. Date: Dec. 3, 2015

(65) Prior Publication Data
US 2017/0240541 A1    Aug. 24, 2017

(30) Foreign Application Priority Data
May 28, 2014    (EP) ..................................... 14170156

(51) Int. Cl.
C07D 417/14    (2006.01)
(52) U.S. Cl.
CPC .................. C07D 417/14 (2013.01)
(58) Field of Classification Search
CPC .................................................. C07D 417/14
USPC ........................................................ 546/209
See application file for complete search history.

(56) References Cited

U.S. PATENT DOCUMENTS

| 8,349,870 B2 * | 1/2013 | Kamireddy | C07D 417/14 514/326 |
|---|---|---|---|
| 2010/0286147 A1 | 11/2010 | Hanagan et al. | |
| 2010/0292275 A1 | 11/2010 | Kamireddy et al. | |
| 2012/0190689 A1 | 7/2012 | Lim et al. | |

FOREIGN PATENT DOCUMENTS

| WO | WO-2004/041793 | 5/2004 |
| WO | WO-2004/058760 | 7/2004 |
| WO | WO-2004/102459 | 11/2004 |
| WO | WO-2006/126171 | 11/2006 |
| WO | WO-2007/056170 | 5/2007 |
| WO | WO-2008/006561 | 1/2008 |
| WO | WO-2008/013622 | 1/2008 |
| WO | WO-2010/001220 | 1/2010 |
| WO | WO-2010/009319 | 1/2010 |
| WO | WO-2013/004551 | 1/2013 |
| WO | WO-2013/098229 | 7/2013 |

OTHER PUBLICATIONS

Ahangar, N. et al. (Nov. 15, 2011). "1-[(2-Arylthiazol-4-yl)methyl]azoles as a New Class of Anticonvulsants: Design, Synthesis, In vivo Screening, and In silico Drug-like Properties," *Chem Bio Drug Des* 78(5): 844-852.
Extended European Search Report dated on Jul. 30, 2014, for EP Patent Application No. 14170156.5 filed on May 28, 2014, 7 pages.
International Search Report dated on Jul. 28, 2015, for PCT Patent Application No. PCT/EP2015/061455 filed on May 28, 2014, 7 pages.
Nam, S. W. et al. (Mar. 25, 2011). "Synthesis and Antifungal Activity of 5-[2-(Alkylaino)pyrimidin-4-yl]-4-phenylthiazol-2cycloalkylamine Derivatives on *Phytophthora capsici*," *Journal of the Korean Society for Applied Biological Chemistry* 54(3): 395-402.

* cited by examiner

*Primary Examiner* — Rita J Desai
(74) *Attorney, Agent, or Firm* — Morrison & Foerster LLP

(57) ABSTRACT

The present invention relates to a novel process for preparing thiazole derivatives.

11 Claims, No Drawings

PROCESS FOR PREPARING THIAZOLE DERIVATIVES

CROSS REFERENCE TO RELATED APPLICATIONS

This application is the national stage of International Application No. PCT/EP2015/061455, filed internationally on May 22, 2015, which claims the benefit of European Application No. 14170156.5, filed May 28, 2014, the disclosures of which are hereby incorporated by reference in their entireties for all purposes.

The present invention relates to a novel process for preparing thiazole derivatives.

Thiazoles are valuable precursors of e.g. fungicidally active ingredients (J. Korean Soc. Appl. Biol. Chem.54(3), 395-402 (2011) or WO 2013/098229) or drugs like anticancer HDAC-inhibitors (WO 2008/006561).

A well-known method for the synthesis of such thiazoles is the so called Hantzsch reaction where a thioamide is reacted with an alpha-haloketone.

However the halo-ketones required for this synthesis are highly reactive species reacting also with any other nucleophile. For this reason thioamides containing a primary or secondary amine have to be used in protected form (for example as an amide or carbamate: the Boc-protecting group WO 2007/56170, WO 2010/001220) to achieve good yields. The additional protection and deprotection steps required for this are not desirable for a technical production.

It is well documented that where a primary or secondary amine is not protected as an amide or carbamate and is therefore available to react the yields are reduced, for example in WO 2004/58760 (44%), WO 2010/93191 (21%), WO 2013/4551 (42%) or WO 2004/102459 (12%). This is also the case if the starting materials of the reaction described hereinafter are submitted to the "classical" Hantzsch synthesis.

Furthermore it is known, that a primary or secondary amine, like piperidine, can be alkylated at the nitrogen atom by reaction with a compound of formula (III) (see page 3), for example in WO 2004/41793, WO 2006/126171 or US 2012/190689.

In the light of the prior art described above, it is an object of the present invention to provide a process that on the one hand does not afford additional protection/deprotection steps and on the other hand gives the desired product in high yield.

The object described above was achieved by a process for preparing thiazoles of the formula (I),

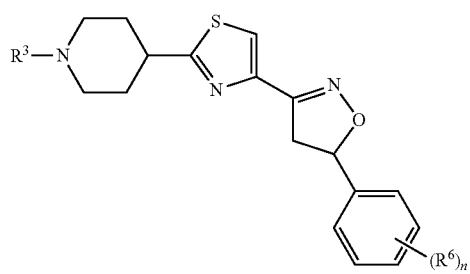

in which
$R^3$ is hydrogen or $C(O)CH_2R^4$;
$R^4$ is halogen, $C_1$-$C_4$-alkylsulfonyloxy or substituted heteroaryl;
$R^6$ is independently of one another halogen or $C_1$-$C_4$-alkylsulfonyloxy;
n is 0, 1, 2, 3
characterized in that compounds of formula (II),

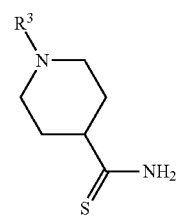

in which
$R^3$ is as defined above
are reacted with compounds of formula (III)

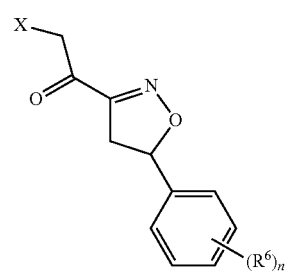

in which
$R^6$ is as defined above;
X is halogen;
in the presence of an acid to form compounds of formula (I).

Preferred is a process according to the invention, where the radicals in formula (I), (II) and (III) are defined as follows:
$R^3$ is hydrogen or $C(O)CH_2R^4$;
$R^6$ is independently of one another chlorine and methylsulphonyloxy;
$R^4$ is fluorine, chlorine, bromine, methylsulfonyloxy, ethylsulfonyloxy, n-propylsulfonyloxy, iso-propysulfonyloxy, n-butylsulfonyloxy, tert-butylsulfonyloxy;
n is 2;
X is bromine or chlorine;

More preferred is a process according to the invention, where the radicals in formula (I), (II) and (III) are defined as follows:
$R^3$ is hydrogen or $C(O)CH_2R^4$;
$R^6$ is independently of one another chlorine and methylsulphonyloxy;
$R^4$ is chlorine, bromine, methylsulfonyloxy
n is 2;
X is chlorine.

Surprisingly, the thiazoles of the formula (I) can be prepared under the inventive conditions with good yields and in high purity, which means that the process according to the invention overcomes the abovementioned disadvantages of the preparation processes previously described in the prior art.

A further aspect of the present invention is compound of formula (I) and salts thereof in which $R^3$ and $R^6$ are as defined above.

General Definitions

Optionally substituted groups may be mono- or polysubstituted, where the substituents in the case of polysubstitutions may be the same or different.

In the definitions of the symbols given in the above formulae, collective terms were used which are generally representative of the following substituents:

Halogen: fluorine, chlorine, bromine and iodine and preferably fluorine, chlorine, bromine and more preferably chlorine.

Alkyl: saturated, straight-chain or branched hydrocarbyl radicals having 1 to 4 carbon atoms, for example (but not limited to) $C_1$-$C_4$-alkyl such as methyl, ethyl, propyl, 1-methylethyl, butyl, 1-methylpropyl, 2-methylpropyl, 1,1-dimethylethyl. This definition also applies to alkyl as part of a composite substituent, for example alkylsulphonyl, alkoxy.

Heteroaryl groups in the context of the present invention, unless defined differently, are aromatic hydrocarbyl groups which have one, two or more heteroatoms selected from O, N, P and S. The definition $C_{6-18}$-aryl encompasses the widest range defined herein for an aryl group having 5 to 18 skeleton atoms, where the carbon atoms are at least once exchanged for heteroatoms. Specifically, this definition encompasses, for example, the meanings of 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5 -yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

PROCESS DESCRIPTION

The process is illustrated in Scheme 1:

Scheme 1:

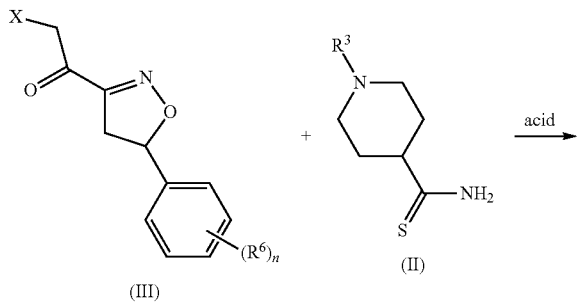

(III)    (II)

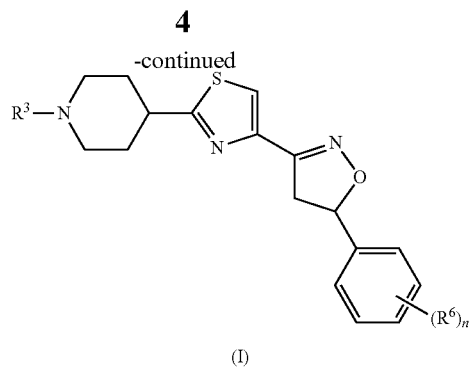

(I)

Compounds of the formula (II) are reacted, in the presence of an acid with compounds of the formula (III) to yield compounds of the formula (I). The compound of formula (II) can also be used in the form of a salt, e.g. as the corresponding hydrochloride.

Examples of inorganic acids are hydrohalic acids, such as hydrogen chloride, hydrogen bromide and hydrogen iodide, sulfuric acid, phosphoric acid and nitric acid, and acidic salts, such as $NaHSO_4$ and $KHSO_4$. Useful organic acids include, for example, carbonic acid and alkanoic acids such as acetic acid, trifluoroacetic acid, trichloroacetic acid and propionic acid, and also glycolic acid, citric acid, benzoic acid, cinnamic acid, oxalic acid, alkylsulphuric monoesters, alkylsulphonic acids (sulphonic acids having straight-chain or branched alkyl radicals having 1 to 20 carbon atoms), arylsulphonic acids or aryldisulphonic acids (aromatic radicals, such as phenyl and naphthyl, which bear one or two sulphonic acid groups), alkylphosphonic acids (phosphonic acids having straight-chain or branched alkyl radicals having 1 to 20 carbon atoms) or arylphosphonic acids. Preferred are HCl, HBr or acetic acid, most preferred is HCl.

Furthermore the process according to the invention can be performed in the presence of a solvent. Examples of solvents are virtually all inert organic solvents. These preferably include aliphatic and aromatic, optionally halogenated hydrocarbons, such as pentane, hexane, heptane, cyclohexane, methyl cyclohexane, petroleum ether, benzine, ligroin, benzene, toluene, xylene, methylene chloride, ethylene dichloride, chloroform, carbon tetrachloride, chlorobenzene and o-dichlorobenzene, ethers such as diethyl ether, methyl tert-butyl ether and dibutyl ether, glycol dimethyl ether and diglycol dimethyl ether, methyltetrahydrofuran, tetrahydrofuran and dioxane, ketones such as acetone, methyl ethyl ketone, methyl isopropyl ketone and methyl isobutyl ketone, esters, such as methyl acetate, ethyl acetate and butyl acetate, nitriles, for example acetonitrile, propionitrile and butyronitrile, alcohols, for example methanol, ethanol, propanol, iso-propanol, butanol, tert-butanol, amides, for example dimethylformamide, dimethylacetamide and N-methylpyrrolidone, and also dimethyl sulphoxide, tetramethylenesulphone and hexamethylphosphoramide and DMPU. Preferred are alcohols or acetonitrile, most preferred are ethanol or iso-propanol.

The reaction is effected at temperatures of −20° C. to +160° C., preferably at temperatures of −5° C. to +150° C., more preferably at 20 to 100° C. and under standard pressure.

The reaction time is not critical and may, according to the batch size and temperature, be selected within a range between a few minutes and several hours.

According to the invention, 1 to 5 mol of the acid is reacted with one mol of compound of the formula (II).

For the process according to the invention 1 to 2 mol, preferred 1 to 1,5 mol, most preferred 1 to 1,2 mol of compound of the formula (II) is reacted with 1 mol of the compound of formula (III).

Alternatively compounds of the formula (II), where in case R³ is hydrogen, can be treated with an acid to form the corresponding salts prior to the reaction with compounds of the formula (III).

Compounds of the formula (II) can be prepared as described in Scheme 2.

Scheme 2

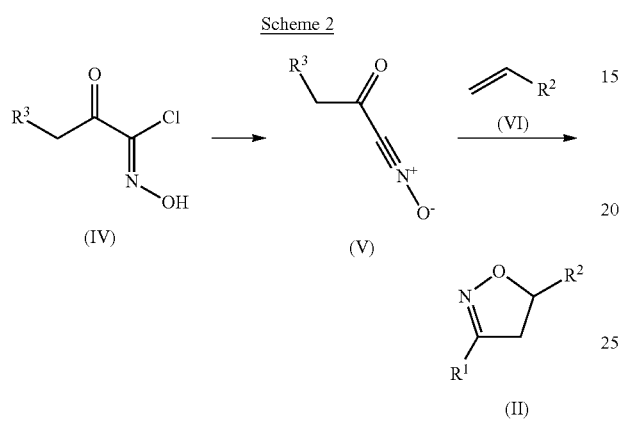

Hydroxyiminochlorides of the formula (IV), are reacted via an elimination reaction to compounds of formula (V) which are in situ transformed to compounds of formula (II) after the addition of (VI) in the presence of a base, an acid and a solvent in acidic pH.

For the reaction according to the invention it is decisive to control the pH level. The reaction is conducted under acidic conditions by addition of a buffer system or by addition of a weak base to capture spontaneously eliminated HCl thereby ensuring that no further deprotonation of compounds of formula (VI), (V) or (II) occurs. Preferably the pH level is between pH 3 and pH 5, more preferably it is between pH 3.5 and pH 4.5.

The weak base can be for example taken from the group of hydrogen carbonates, like sodium hydrogencarbonate or potassium hydrogencarbonate, or from the group of hydrogenphosphates, like (di)sodium (di)hydrogenphosphate or(di)potassium (di)hydrogenphosphate or from the group of alkali salts of organic acids, like sodium acetate or sodium benzoate. Preferred is sodium hydrogencarbonate The buffer system consists of a weak acid and a salt of the weak acid, it can be for example taken from acetic acid/sodium acetate or acetic acid/ammonium acetate or formic acid/sodium formiate or dihydrogenphosphate/monohydrogenphosphate. Preferred is acetic acid/sodium acetate.

The reaction can be performed in a solvent, taken from the group of halogenalkanes like methylene chloride or 1,2-dichloroethane or from the group of aromatic compounds like benzene, toluene, xylene, chlorobenzene, dichlorobenzene or from the group of polar aprotic solvents like N,N-dialkylformamide, -acetamide, N-methylpyrrolidon, dimethylpropylene urea, tetramethyl urea or in nitriles like acetonitriles, propionitrile or butyronitrile, in alkohols like methanol, ethanol, n-propanol, iso-propanol, n-butanol or iso-butanol, in ethers like diethylether, tert.butylmethylether, diisopropylether, in ketones like acetone, methylisobutyl ketone in carboxylic esters like ethyl acetate, butyl acetate. Preferable the reaction can be performed in acetonitrile or ethyl acetate. The reaction can be performed in mixtures of these solvents. Advantageously, can the reaction be performed in the presence of water.

The reaction can be performed in a temperature range from −10° C. to the boiling point of the solvent, which is used, preferable in the range from 0° C. to 50° C., more preferable in the range from 5° C. to 40° C.

Compounds of formula (IV) are known and can be prepared as described in J. Org. Chem. 45, 3916 (1980) or U.S. Pat. No. 5,064,844.

Compounds of formula (VI) are well known. They are either commercially available or can be prepared according procedures described in standard literature like "Organic Synthesis" ("OS"), for example in OS 1928, 8, 84 ; OS 1948, 28, 31; OS 1953, 33, 62; OS 1966, 46, 89; OS 2006, 83, 45.

EXAMPLE

The invention is illustrated by the following examples:

Preparation of 4-[4-(5-{2-chloro-6-[(methylsulfonyl)oxy]phenyl}-4,5-dihydro-1,2-oxazol-3-yl)-1,3-thiazol-2-yl]piperidinium chloride

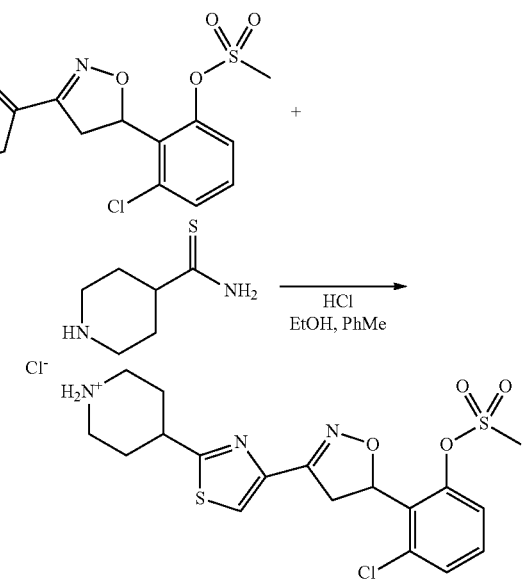

93 g (0.264 mol) of 3-chloro-2-[3-(chloroacetyl)-4,5-dihydro-1,2-oxazol-5-yl]phenyl methanesulfonate were suspended in 930 ml of ethanol. 26 g of 37% hydrochloric acid and 42 g (0.291 mol) of piperidine-4-carbothioamide are added and the mixture is heated to 70° C. and stirred for 4 hours. After forming an intermediate clear solution the product precipitates. 930 g of solvent is distilled off under vacuum at 50 to 60° C., while 930 ml of toluene is added. The suspension is cooled to 5° C., the product is filtered off, washed with toluene and dried at 45° C. in vacuum.

98.4 g of 4-[4-(5-{2-chloro-6-[(methylsulfonyl)oxy]phenyl}-4,5-dihydro-1,2-oxazol-3-yl)-1,3-thiazol-2-yl]piperidinium chloride with a purity of 99% is received (yield: 90%).

Preparation of 3-chloro-2-(3-{2-[1-(chloroacetyl)piperidin-4-yl]-1,3-thiazol-4-yl}-4,5-dihydro-1,2-oxazol-5-yl)phenyl methanesulfonate

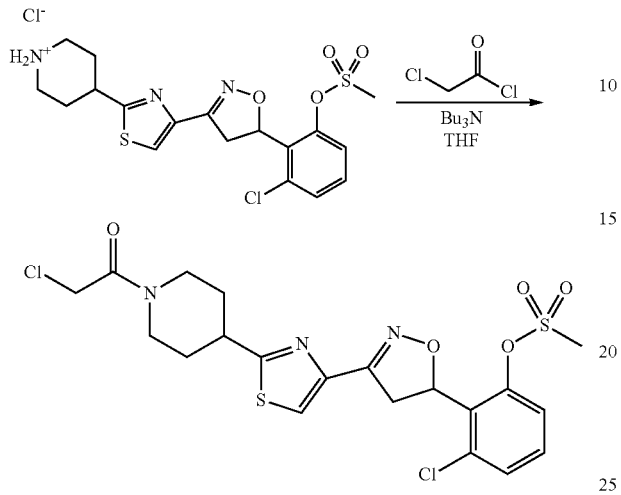

40 g (0.083 mol) of 4-[4-(5-{2-chloro-6-[(methylsulfonyl)oxy]phenyl}-4,5-dihydro-1,2-oxazol-3-yl)-1,3-thiazol-2-yl]piperidinium chloride is suspended in 300 ml of THF. 55 g (0.096 mol) of tributylamine is added and the mixture is warmed to 45° C. and stirred for 15 minutes. A solution of 16.6 g (0.147 mol) of chloro acetylchloride in 20 ml of THF is added over 2 hours. During that time the mixture forms a dark solution. After 30 min stirring the mixture is cooled to 20° C. and poured on a solution of 17.6 g 20% hydrochloric acid in 320 ml cold water. Then 320 ml of water is added over 1 hour to the mixture at 25° C. With intermediate seeding the product cristallises. It is filtered off, washed with water and dried at 45° C. in vacuum.

38.3 g of 3-chloro-2-(3-{2-[1-(chloroacetyl)piperidin-4-yl]-1,3-thiazol-4-yl}-4,5-dihydro-1,2-oxazol-5-yl)phenyl methanesulfonate with a purity of 97% is received (yield: 85%).

Preparation of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate

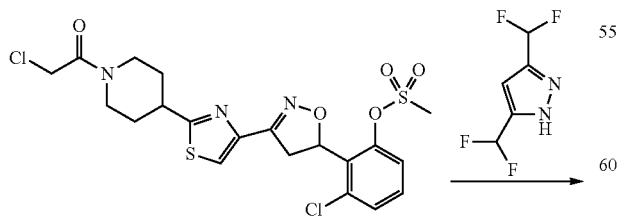

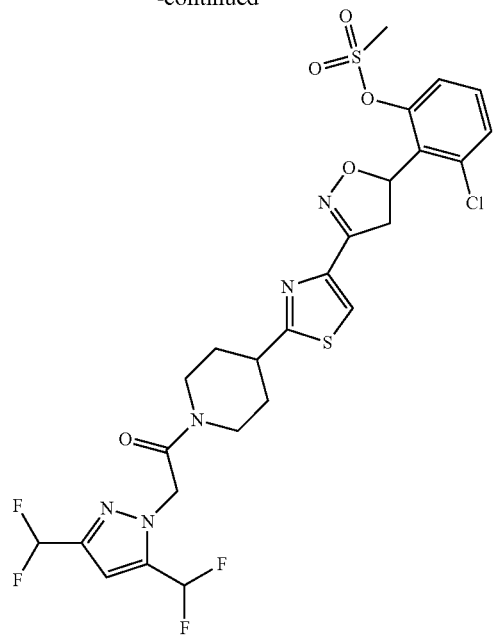

16 g (0.03 mol) of of 3-chloro-2-(3-{2-[1-(chloroacetyl)piperidin-4-yl]-1,3-thiazol-4-yl}-4,5-dihydro-1,2-oxazol-5-yl)phenyl methanesulfonate, 5,7 g (0.033 mol) 3,5-bis(difluoromethyl)-1H-pyrazole, 4.9 g (0.046 mol) sodium carbonate and 1.5 g (0.005 mol) tetrabutylammonium bromide are suspended in 100 ml acetonitrile. The mixture is heated up to 70° C. and stirred for 3.5 hours. At 40° C. most of the solvent is distilled off in vacuum and replaced by 100 ml of toluene. The mixture is cooled to 20° C., stirred for 1 hour, seeded and then cooled to 5° C. and stirred for 1 hour. A mixture of 20 ml of water and 6 ml 20% HCl is added and stirred for 30 minutes. The solid is filtered off, washed with toluene and water and dried at 45° C. in vacuum.

18 g of 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate with a purity of 94% is received (yield: 84%).

The invention claimed is:
1. A process for preparing a compound of formula (I),

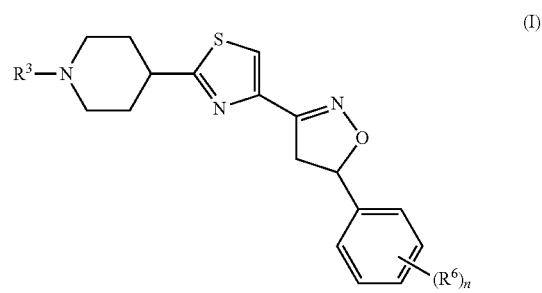

wherein:
R³ is hydrogen;
each R⁶ is independently halogen or $C_1$-$C_4$-alkylsulfonyloxy; and
n is 0, 1, 2, or 3;
comprising reacting a compound of formula (II) or a salt thereof,

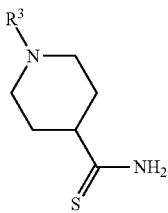

wherein:
R³ is as defined for the compound of formula (I);
with a compound of formula (III),

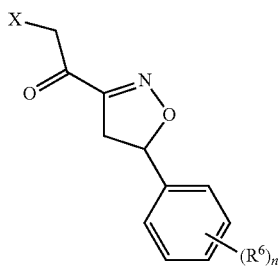

wherein:
R⁶ and n are as defined for the compound of formula (I); and

X is halogen;
in the presence of an acid to form the compound of formula (I).

2. The process according to claim 1, wherein:
R³ is hydrogen;
each R⁶ is independently chlorine or methylsulphonyloxy;
n is 2; and
X is bromine or chlorine.

3. The process according to claim 1, wherein:
R³ is hydrogen;
each R⁶ is independently chlorine or methylsulphonyloxy;
n is 2; and
X is chlorine.

4. The process according to claim 1, wherein the compound of formula (II) is used in form of a salt.

5. The process according to claim 1, wherein the compound of formula (II) is used in form of a hydrochloride salt.

6. The process according to claim 1, wherein the acid is HCl or HBr.

7. The process according to claim 1, wherein the acid is HCl.

8. The process according to claim 1, wherein the process is performed in the presence of a solvent.

9. The process according to claim 8, wherein the solvent is an alcohol.

10. The process according to claim 8, wherein the solvent is ethanol or iso-propanol.

11. The process according to claim 1, wherein the amount of acid is one to five moles per one mole of the compound of formula (II).

* * * * *